(12) United States Patent
Fix et al.

(10) Patent No.: US 9,404,886 B2
(45) Date of Patent: Aug. 2, 2016

(54) MICROELECTROCHEMICAL SENSOR AND METHOD FOR OPERATING A MICROELECTROCHEMICAL SENSOR

(71) Applicant: Robert Bosch GmbH, Stuttgart (DE)

(72) Inventors: Richard Fix, Gerlingen (DE); Denis Kunz, Untergruppenbach (DE); Andreas Krauss, Tuebingen (DE); Kathy Sahner, Leonberg (DE); Philipp Nolte, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 277 days.

(21) Appl. No.: 14/196,142

(22) Filed: Mar. 4, 2014

(65) Prior Publication Data

US 2014/0262838 A1 Sep. 18, 2014

(30) Foreign Application Priority Data

Mar. 12, 2013 (DE) .................. 10 2013 204 197

(51) Int. Cl.
*G01N 27/407* (2006.01)
*G01N 27/406* (2006.01)

(52) U.S. Cl.
CPC ........ *G01N 27/4072* (2013.01); *G01N 27/4067* (2013.01)

(58) Field of Classification Search
CPC . G01N 27/403; G01N 27/406; G01N 27/407; H01G 9/00
See application file for complete search history.

(56) References Cited

U.S. PATENT DOCUMENTS

| | | | | |
|---|---|---|---|---|
| 4,765,864 A | * | 8/1988 | Holland | H01G 9/00 204/242 |
| 4,874,500 A | * | 10/1989 | Madou | G01N 27/403 204/408 |
| 5,368,704 A | * | 11/1994 | Madou | A61M 31/002 204/224 M |

FOREIGN PATENT DOCUMENTS

DE   199 41 051 A1   3/2001

* cited by examiner

*Primary Examiner* — Jennifer Dieterle
(74) *Attorney, Agent, or Firm* — Maginot, Moore & Beck LLP (57) ABSTRACT

A microelectrochemical sensor having a diaphragm, a web, a first and a second electrode. The diaphragm is permeable to ions of a chemical species, is arranged transversely with respect to a cutout in a base body, and closes off the cutout in a fluid-tight fashion. The web is arranged on a first side of the diaphragm between a first partial surface and a second partial surface, and is designed to adjust a temperature of the diaphragm to an operating temperature using electrical energy. The first electrode has a first partial electrode and a second partial electrode, is permeable to fluid, and is arranged on the first side of the diaphragm. The web prevents electrical contact between the first electrode and the diaphragm. The second electrode has a third partial electrode and a fourth partial electrode, is also permeable to fluid, and is arranged on a second side of the diaphragm.

14 Claims, 7 Drawing Sheets

MICROELECTROCHEMICAL SENSOR AND METHOD FOR OPERATING A MICROELECTROCHEMICAL SENSOR

This application claims priority under 35 U.S.C. §119 to patent application no. DE 10 2013 204 197.7, filed on Mar. 12, 2013 in Germany, the disclosure of which is incorporated herein by reference in its entirety.

The present disclosure relates to a microelectrochemical sensor, to a method for operating a microelectrochemical sensor and to a corresponding computer program product.

BACKGROUND

In order to be able to adapt a ratio between a quantity of fuel for accomplishing a combustion process and an available quantity of oxygen, definitive information is required about an oxygen concentration in an exhaust gas of the combustion process. Since the exhaust gas usually has a high temperature at a measuring point, a temperature-resistant sensor is necessary to determine the oxygen concentration.

DE 199 41 051 A1 describes a sensor element for determining the oxygen concentration in gas mixtures and a method for manufacturing same.

SUMMARY

Against this background, the present disclosure presents a microelectrochemical sensor, a method for operating a microelectrochemical sensor, and also a method for manufacturing a thin layer and finally a corresponding computer program product.

In order to adjust the temperature of a sensor surface of a microelectrochemical sensor, electrical energy is necessary which is converted by a heater into thermal energy and is output to the sensor surface. The temperature of a base body of the sensor can be adjusted in the region of the sensor surface. The temperature of the diaphragm can be adjusted by conducting heat from the base body to the diaphragm.

In order, in contrast to the above, to save energy and nevertheless be able to adjust the temperature of as large a sensor surface as possible, the heater can be arranged on the sensor surface without making electrical contact with the sensor surface. The heater can be decoupled from a base body of the microelectrochemical sensor. As a result, the temperature of the sensor surface can be adjusted directly. Changes in the ambient temperature at the sensor surface can be compensated directly and quickly by the heater without the base body as an inert, damping mass.

A microelectrochemical sensor having at least the following features is presented:
a diaphragm which has a first partial surface and a second partial surface, wherein the diaphragm is permeable to ions of a specific chemical species, at least in the region of the first partial surface and of the second partial surface, wherein the diaphragm is arranged transversely with respect to a cutout in a base body and closes off the cutout in a fluid-tight fashion;
a web which is arranged on a first side of the diaphragm between the first partial surface and the second partial surface, wherein the web is designed to adjust the temperature of the diaphragm in the region of the first partial surface and of the second partial surface to an operating temperature using electrical energy;
a first electrode having a first partial electrode and a second partial electrode, wherein the first electrode is permeable to fluid and is arranged on the first side of the diaphragm, at least on the first partial surface and the second partial surface, wherein the web is designed to prevent electrical contact between the first electrode and the diaphragm in the region of the web; and
a second electrode having a third partial electrode and a fourth partial electrode, wherein the second electrode is permeable to fluid and is arranged on a second side of the diaphragm, at least on the first partial surface and the second partial surface.

A diaphragm can be understood to be a thin layer of material. The diaphragm can be composed of various materials. Partial surfaces of the diaphragm can represent a sensor surface of the sensor. The diaphragm can have a ceramic material at least in the partial surfaces. The diaphragm or the partial surfaces can be fluid tight. The diaphragm or the partial surfaces can be selectively permeable. The diaphragm or the partial surfaces can be equipped with a catalyst. The diaphragm or the partial surfaces can ionize the chemical species through a catalyst on, and alternatively or additionally in, the diaphragm or the partial surfaces. A base body can have a semiconductor material and alternatively or additionally a ceramic material. The base body can have electrical contacts for making contact with the sensor. A cutout can be a through-hole or a cavity. A web can be a fin. The web can be branched. The web can have a material of the base body. The web can be decoupled from the base body. The web can be designed to stiffen the diaphragm. The web can be designed to adjust the temperature of the diaphragm by means of dissipated heat at an electrical resistance. The operating temperature can be an ionization temperature of the chemical species at the diaphragm. The first electrode can make contact exclusively with the diaphragm next to the web. The first electrode can be divided into partial electrodes. The second electrode can also be divided into partial electrodes. The partial electrodes can adjoin one another. The electrodes can be porous. The electrodes are electrically conductive. The electrodes can be equipped with a catalyst. The partial surfaces can be in contact with the electrodes on both sides.

Furthermore, a method for operating a sensor according to the approach presented here is presented, wherein the method has the following step:
applying an electrical voltage between the first electrode and the second electrode in order to pump ions of the chemical species through the diaphragm.

As a result of application of a voltage to the electrodes, the ions can be conveyed through the diaphragm. A direction of conveyance can be determined by a polarity of the voltage. A high pressure can be generated in a closed-off volume by applying the voltage since no mechanical parts have to be moved in order to generate the pressure and no appreciable clearance losses occur. When the voltage is applied, the chemical species can be produced in a pure form on one of the sides of the diaphragm. On the other side, the species can also be removed from chemical compounds if the diaphragm is equipped in an ionizing fashion or the compounds are already present in an ionized form.

The method can have a step of detecting a change in a capacitance between the first electrode and a third electrode in order to determine a deflection of the diaphragm by using the change. The third electrode can be arranged in a chamber or cavity which is closed off in a fluid-tight fashion at the diaphragm. Through a difference in pressure between a pressure on the first side of the diaphragm and on the second side of the diaphragm, the diaphragm can be pushed out of a position of rest toward the third electrode or away from the third electrode. As a result of a changed distance between the electrodes, a change occurs in an electrical capacitance of a capacitor which is formed from the first electrode and the third electrode. In this context, a quantity of charge which can be stored by the capacitor can rise if the distance between the electrodes decreases. The distance influences the capacitance approximately linearly.

The method can have a step of determining a pressure on the diaphragm by using the deflection. The pressure can be a resulting difference in pressure between a first absolute pressure on the first side of the diaphragm and a second absolute pressure on the second side of the diaphragm. The diaphragm is deformed by the difference in pressure. The pressure can be determined by using stored mechanical properties of the diaphragm.

The electrical voltage can be applied for a predetermined period. Alternatively or additionally, the voltage can be applied until the deflection is greater than a predetermined value. Damage to the diaphragm can be avoided by limiting the duration and alternatively or additionally limiting the deflection. The voltage can be applied again after a predetermined pause. The voltage can also be applied again if the deflection is smaller than a further predetermined value.

The method can have a measuring step in which the electrical voltage between the first electrode and the second electrode is measured in order to detect a first ratio of a first concentration of ions at the first electrode to a second concentration of ions at the second electrode. Alternatively or additionally, the electrical voltage between the third electrode and the fourth electrode can be measured in order to detect a second ratio of the first concentration of ions at the third electrode to a third concentration of ions at the fourth electrode. The voltage can be measured if no pump voltage is applied. In the case of electrode pairs which can be switched independently of one another, the pump voltage can be applied to the first and second electrodes, while the voltage between a third and a fourth electrode is detected. Conversely, the pump voltage can be applied to the third and the fourth electrodes, while the voltage between the first and second electrodes is detected. In particular, one of the diaphragms can have a diffusion point. Atoms can diffuse through the diffusion point as a result of the increased pressure in the cavity. As a result, concentrations of other chemical species between the diaphragms can be reduced below a detection threshold by pumping, even pumping at intervals. A reference fluid can then be made available by the pump voltage, and an absolute concentration of one of the chemical species in a fluid to be measured can be determined using the reference fluid.

In addition, a method for manufacturing a thin layer with a predetermined layer thickness is presented, wherein the method has the following steps:
making available a first electrode, wherein the electrode extends at least over a partial region of the thin layer;
depositing a first partial layer of the thin layer is deposited on a surface of the thin layer, wherein the first partial layer is deposited more thinly than the predetermined layer thickness;
measuring a current layer thickness of the thin layer taking into account the first electrode and a second electrode, wherein the second electrode is temporarily arranged directly on a side of the thin layer lying opposite the first electrode; and
depositing a second partial layer on the first partial layer, wherein the second partial layer is deposited with a residual layer thickness which is determined using the current layer thickness and the predetermined layer thickness, in order to produce the thin layer with the predetermined layer thickness.

Depositing can be understood here to mean resublimating or condensing. The depositing can also occur chemically, for example through precipitation. The depositing can also occur by using a gas phase deposition process. For example, a chemical, and alternatively or additionally a physical, gas phase deposition process can be used. A current layer thickness can be determined electrically. The second electrode can be deposited on the thin layer in order to determine the current layer thickness very precisely. The second electrode can also be printed onto the thin layer. As a result, the second electrode can easily be removed again.

The web can be embodied as a grid. The first partial surface and the second partial surface can be enclosed by the web. The partial surfaces can also form a grid. A size of the partial surfaces can be limited by the grid, in order to acquire stability. A plurality of partial surfaces can make available a large overall surface as a sensor surface. The first partial electrode can be electrically connected to the second partial electrode. The third partial electrode can be electrically connected to the fourth partial electrode. The first electrode on the first side can enclose the web, with the result that the web is arranged between the first electrode and the diaphragm. The partial electrodes on one side of the diaphragm can be at a common electrical potential. As a result, just one individual connecting line to the base body is necessary for each side of the diaphragm.

The diaphragm can have an insulating region which extends around the cutout and which is electrode-free. The insulating region can be embodied, in particular, in an annular shape here and run all around the cutout. The insulating region can be composed of a material of the diaphragm and alternatively or additionally an insulating material. The insulating region can form an edge around the partial surfaces. The insulating region can be arranged between the base body and the partial surfaces. The insulating region can insulate the partial surfaces thermally and alternatively or additionally electrically from the base body. Energy consumption for adjusting the temperature of the diaphragm can be reduced by means of the insulating region.

The web can have for the purpose of adjusting the temperature a heating element, which is arranged between the web and the diaphragm and is alternatively or additionally arranged between the first electrode and the web and is electrically insulated from the first electrode and the diaphragm. Alternatively, a material of the web can have an electrical resistance, wherein the material of the web is insulated from the first electrode and alternatively or additionally the diaphragm. An electrical resistance can be an ohmic resistance. Electrical energy can be converted into thermal energy at the resistance.

Contact can be made with the first electrode via a first conductor track. Contact can be made with the second electrode via a second conductor track. Contact can be made with the heating element via a third conductor track and a fourth conductor track. The conductor tracks can run via the insulating region to the base body and can be alternatively or additionally electrically insulated from the diaphragm.

Conductor tracks can be electrically conductive and can have a small ohmic resistance. The conductor tracks can be flexible. For example, the conductor tracks can have meanders in order to be able to absorb tensile loads and alternatively or additionally bending loads.

The conductor tracks can be oriented, at least over a partial distance, tangentially with respect to an edge of the cutout. The conductor tracks can be insulated from the diaphragm by means of one fin each. Alternatively or additionally, the conductor tracks can be embedded in an insulating material. A tangential arrangement of the conductor tracks can result in particularly small bending torques in the conductor tracks. A fin can be a prolongation of the web over the insulating region to the base body. The fin can be made of the same material as the web. A plurality of conductor tracks can be arranged closely one next to the other by means of an insulating material.

The sensor can have a device for detecting a change in distance and the change in distance between the diaphragm and a further part of the sensor. Alternatively or additionally, the sensor can have a temperature sensor for detecting a temperature of the diaphragm and alternatively or additionally an ambient temperature. A device for detecting the distance can be a capacitive sensor which, depending on the change in distance, can make available an electrical signal. A deflection of the diaphragm can be detected by the detecting device. A difference in pressure across the diaphragm can be determined from the deflection. A temperature sensor for detecting a temperature of the diaphragm can be arranged on the diaphragm and can be connected to the base body via conductor tracks. The temperature sensor can be arranged on the second side of the diaphragm. A temperature sensor for detecting an ambient temperature can be arranged at a minimum distance from the diaphragm. Chemical species, to which the partial surfaces are impermeable, can be detected by the temperature sensors.

The cutout can be embodied as a closed-off chamber. A wall of the chamber, lying opposite the diaphragm, can have a third electrode. The diaphragm can be used as a pressure sensor by means of a chamber which is closed off from the surroundings. By actively pumping ions through the diaphragm it is possible to test the tightness of the chamber. By means of a third electrode, it is possible to form a variable capacitance with the first electrode and alternatively or additionally the second electrode, via which variable capacitance a change in a distance between the electrodes can be detected.

The wall lying opposite can be embodied as a further diaphragm. The further diaphragm can have a further web and a fourth electrode according to the approach presented here. When there are two independently usable diaphragms, one of the diaphragms can be used to make available a reference fluid composed of 100% of the chemical species. The diaphragms can be arranged freely in the chamber. The second diaphragm can be used to determine an absolute content of the species in a surrounding fluid.

The chamber can have a diffusion opening. A diffusion opening may be so small that the fluid can pass through only at a diffusion speed. Atoms and molecules of the fluid from the chamber can escape through the diffusion opening. If ions of the species are actively conveyed into the chamber, no extraneous atoms or extraneous molecules from outside the species may be located in the chamber after a certain time.

A computer program product having a program code which can be stored on a machine-readable carrier such as a semiconductor memory, a hard disk memory or an optical memory, and is used to carry out the method according to one of the embodiments described above when the program product is executed on a computer or a device, is also advantageous.

BRIEF DESCRIPTION OF THE DRAWINGS

The disclosure will be explained in more detail below by way of example with reference to the appended drawings, in which.

DETAILED DESCRIPTION

In the following description of preferred exemplary embodiments of the present disclosure, identical or similar reference signs are used for the similarly acting elements illustrated in the various figures, a repeated description of these elements being dispensed with.

Figure 1:
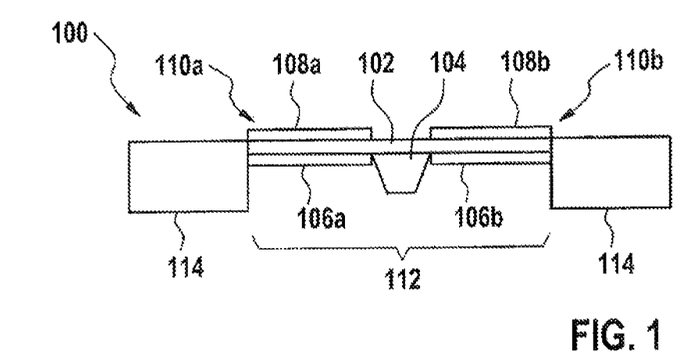
FIG. 1 shows a block circuit diagram of a microelectrochemical sensor according to an exemplary embodiment of the present disclosure.

FIG. 1 shows a block circuit diagram of a microelectrochemical sensor 100 according to an exemplary embodiment of the present disclosure. The microelectrochemical sensor 100 has at least one diaphragm 102, a web 104, a first electrode 106 and a second electrode 108. The diaphragm 102 has a first partial surface 110a and a second partial surface 110b. The diaphragm 102 is permeable to ions of a specific chemical species, at least in the region of the first partial surface 110a and of the second partial surface 110b. The diaphragm 102 is arranged transversely with respect to a cutout 112 in a base body 114 and closes off the cutout 112 in a fluid-tight fashion. The web 104 is arranged on a first side of the diaphragm 102 between the first partial surface 110a and the second partial surface 110b. The web 104 is designed to adjust the temperature of the diaphragm in the region of the first partial surface 110a and of the second partial surface 110b to an operating temperature using electrical energy. The first electrode 106 has a first partial electrode 106a and a second partial electrode 106b. The first electrode 106 is permeable to fluid and is arranged on the first side of the diaphragm 102, at least on the first partial surface 110a and the second partial surface 110b. The web 104 is arranged or designed in such a way to prevent electrical contact between the first electrode 106 and the diaphragm 102 in the region of the web 104. The second electrode 108 has a third partial electrode 108a and a fourth electrode 108b. The second electrode 108 is also permeable to fluid and is arranged on a second side of the diaphragm 102, at least on the first partial surface 110a and the second partial surface 110b.

The approach which is presented here describes various implementation possibilities for solid electrolyte-based sensors 100 for oxygen and nitrogen dioxide, in particular the design of a sensor 100 with an integrated, selectively acting heater which is necessary for operation.

Figure 2:
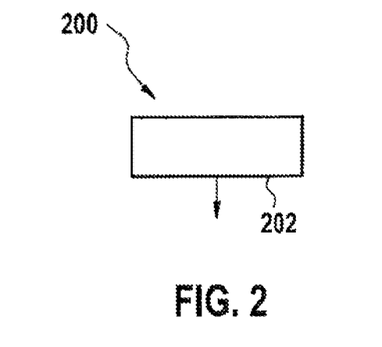
FIG. 2 shows a flowchart of a method for operating a microelectrochemical sensor according to an exemplary embodiment of the present disclosure.

FIG. 2 shows a flowchart of a method 200 for operating a microelectrochemical sensor according to an exemplary embodiment of the present disclosure. The method 200 can be carried out on a microelectrochemical sensor such as is described, for example, in FIG. 1. The method 200 has a step 202 of applying an electrical pump voltage between the first electrode and the second electrode in order to pump ions of the chemical species through the diaphragm.

Figure 3:
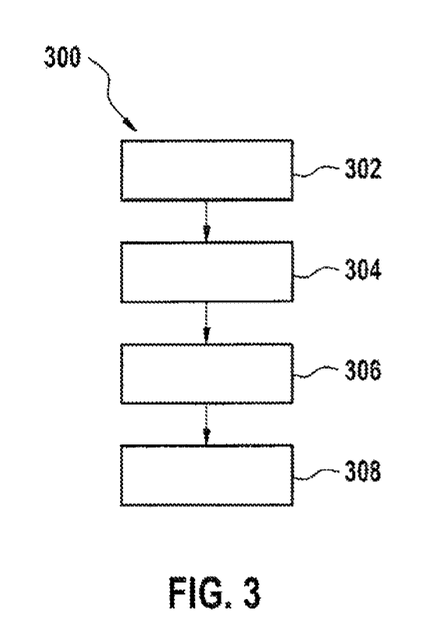
FIG. 3 shows a flowchart of a method for manufacturing a thin layer with a predetermined layer thickness according to an exemplary embodiment of the present disclosure.

FIG. 3 shows a flowchart of a method 300 for manufacturing a thin layer with a predetermined layer thickness according to an exemplary embodiment of the present disclosure. The thin layer can be, for example, a component of a diaphragm of a sensor according to the approach presented here. The method 300 has a making available step 302, a first depositing step 304, a measuring step 306 and a further depositing step 308. In the making available step 302, a diaphragm made of thin layers is made available with a first electrode which extends at least over a partial region of the thin layer. The diaphragm as a first partial layer is deposited more thinly here than the predetermined layer thickness. In the first depositing step 304, a second temporary electrode is deposited on a provided surface of the thin layer. In this context, the second electrode is advantageously arranged directly on a side of the thin layer lying opposite the first electrode, and said second electrode covers only a small area of the thin layer. In the measuring step 306, a current layer thickness of the thin layer is measured using the first electrode and the second temporary electrode. In the further depositing step 308, a second partial layer is then deposited on the first partial layer. The second partial layer is deposited with a residual layer thickness on the entire thin layer, in order to produce the thin layer with the predetermined layer thickness. The residual layer thickness is for this purpose determined using the current layer thickness, the properties measured in step 306 and the predetermined layer thickness.

In other words, FIG. 3 shows a flowchart of a method 300 for manufacturing a microelectrochemical sensor element in which the diaphragm thickness is adjusted in such a way that electrical properties and gas measuring properties are within predefined deviations or are identical with respect to a predefined standard. As a result, the reproducibility is improved.

During the deposition of the thin layers as a functional feature of the sensor, for example by means of pulsed laser deposition or using CVD methods, it is already possible to set such high temperatures in situ during the deposition either permanently or only temporarily, that the layers per se are already ion-conducting. If a first electrode is then already present underneath the deposited material, the ion-conducting material of the diaphragm can be characterized and adjusted with a second, locally limited and, if appropriate, only temporarily applied upper electrode. At the front, the electrode can be formed, for example, by means of a die which is temporarily pressed on or by depositing over a small surface near to the edge an electrode with which electrical contact is then made. The measurement 306 can be carried out by impedance spectroscopy or by measuring the adjustment current.

The deposition is carried out incrementally, a first layer is deposited 304 in such a way that a thickness below a target thickness or a value below an electrical target value is obtained. In a repeated process composed of depositing 308 and measuring 306, the target value is then set given the thickness or the electrical property. Since a different gas can also already be applied to the front and rear sides of the wafers during the deposition of the functional layer, a gas function can already be measured within the scope of the deposition. Furthermore, temperature treatment steps between the deposition and measurement in the wafers in the system are also possible as components of the measurement.

Figure 4:
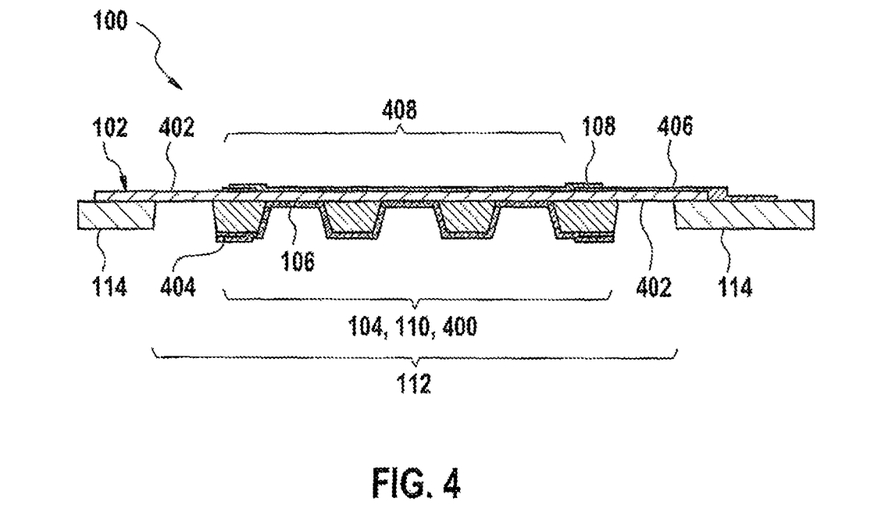
FIG. 4 shows an illustration of a microelectrochemical sensor according to an exemplary embodiment of the present disclosure.

FIG. 4 shows an illustration of a microelectrochemical sensor 100 according to an exemplary embodiment of the present disclosure. The sensor 100 corresponds to the sensor in FIG. 1. For the sake of simplification, all the partial surfaces 110 are characterized uniformly. In addition, the sensor 100 has three further webs 104, which are arranged, like the web in FIG. 1, on the first side of the diaphragm 102. The webs 104 form a coherent fin structure 400. In intermediate spaces between the webs 104, three partial surfaces 110 are arranged one next to the other. The diaphragm 102 has a circumferential region 402 with a thermally insulating carrier diaphragm 102 between the webs 104 and the base body 114. The insulating region 402 insulates the partial surfaces 110 from the base body 114. The diaphragm 102 is arranged on a surface of the base body 114 and extends over the cutout 112 and beyond. The fin structure 400 forms a regular grid. Nine partial surfaces 110 are arranged between the webs 104. The first electrode 106 extends in a continuous layer over the partial surfaces 110 and the fin structure 400, wherein an edge of the fin structure 400 facing the base body 114 is free. The first electrode 106 is embodied in a three-dimensional fashion. A first conductor track 404 is arranged as an electrode terminal for the first electrode 106 on the web 104 which runs around the fin structure 400. The second electrode 108 also extends in a continuous layer over a region of the diaphragm 102 lying opposite the fin structure 400 and the partial surfaces 110. The second electrode 108 is embodied in a planar or two-dimensional fashion. The second electrode 108 is placed in contact with the base body 114 via a second conductor track 406 on the second side of the diaphragm 102.

In other words, FIG. 4 shows a gas sensor 100 which is based on MEMS (microelectromechemical sensor element) and has a solid electrolyte 102. A microelectrochemical sensor element (MECS) is formed from the combination. A solid electrolyte gas sensor can be, for example, an oxygen sensor in the form of the lambda probe. Compared to the ceramic thick layer technology, which requires large minimum dimensions both in terms of structure widths (typically >30 µm) and in terms of layer thicknesses (typically >10 µm), the MEMS-based sensor can be made much smaller. Through the combination of a plurality of cells, it is possible to produce both oxygen sensors and other sensors, for example for nitrogen oxides.

FIG. 4 shows an example of an implementation of a selectively heated arrangement of MECS cells 110 of the heater as a sectional diagram of an arrangement for heating a microelectrochemical sensor element 100 (MECS). The MECS 100 is composed here of a plurality of individual relatively small diaphragms 110 made of oxygen-ion-conducting material. The heater is arranged on webs 104 between the diaphragms 110. The webs 104 distribute the heat uniformly and a circumferential diaphragm ring 402 ensures thermal insulation from the substrate 114. Selective heating is therefore implemented and a low energy requirement of the sensor 100 is made possible.

The sensor 100 can be combined with further sensors or measuring methods in order to increase the measuring accuracy or in order to make further measuring variables possible.

The sequence of the layers of the sensor 100 is characteristic of the approach presented here. An upper electrode 108 is followed by an ion-conducting material (in the form of a diaphragm) 102. This is followed, in the region of the web, by the web 104, an insulating layer, a heater and, in the region of the electrodes, a lower electrode 106, wherein at least the layers for the insulation, heater and web 104 are structured in such a way that individual diaphragms 110 or diaphragm regions 110 are composed of ion-conducting material with which contact is made from above and below by an electrode material. In this context, under the region comprising the insulation, heater and carrier 104 at least one electrode 106 is not in contact with the diaphragm 102.

The MECS sensor 100 is composed of various small individual diaphragms 110. The active regions 110 are constructed from the ion-conducting diaphragm 102 with electrodes 106, 108 which are applied on both sides. In the case of the operating temperature (typically above 400° C.), in the active regions 110 oxygen is either pumped through the ion-conducting material 102 by means of a voltage applied to the electrodes 106, 108, or a difference in potential at the gas-permeable electrodes 106, 108, which can be measured, is produced through differences in concentration of the oxygen on the two sides of the diaphragm 102. Active regions 110 of the diaphragm are not to be covered in an air-tight fashion since a pump current can result in very high pressures which can cause the assembly of layer bonding. For this reason, a potential is applied only to the point 110 of the diaphragm 102 at which a gas flow can take place. This is implemented in FIG. 4 in that the electrodes 106, 108 are not applied until after the individual diaphragms 110 are released, and in that the webs 104 are manufactured from material which is non-conductive even at the high operating temperatures or are electrically insulated from the electrode potential. This insulation can be implemented, for example in the case of the use of Si (silicon) as the substrate material 114, by thermal oxidation, wherein all the surfaces of the Si (even at the side walls of the webs 104) are insulated. This oxidation ideally takes place in a temperature step which can be necessary for conditioning the diaphragm 102.

In FIG. 4, the heated region 408 with individual MECS diaphragms 110 and heater structures of the MECS 100 is thermally insulated from the rest of the substrate 114 by only the ion-conducting diaphragm material 102. Alternatively, it is also possible to use only the insulation layer or both layers together here. Basically, other diaphragm materials can also be used here.

Figure 5:
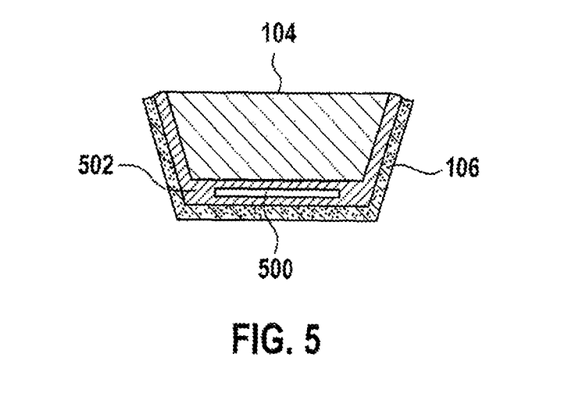
FIG. 5 shows a view of a detail of a web of a microelectrochemical sensor according to an exemplary embodiment of the present disclosure.

FIG. 5 shows a view of a detail of a web 104 of a microelectrochemical sensor 100 according to an exemplary embodiment of the present disclosure. The web 104 corresponds to the webs of the microelectrochemical sensor in FIG. 4. The web 104 is illustrated in an enlarged fashion. In addition, FIG. 5 illustrates an exemplary embodiment of the heating of the partial surfaces using a heating element 500. The heating element 500 is embedded in an edge region 502 of the web 104. For this purpose, a material of the web 104 has been changed in such a way that the edge region 502 is electrically insulating. The edge region 502 faces the first electrode 106. The edge region 502 is completely covered by the first electrode 106. The diaphragm is not illustrated here.

The first electrode 106 extends, as in FIG. 4, to the side of the web 104 on the adjacent partial surfaces of the diaphragm.

FIG. 5 shows as a detail the intermediate region between two MECS diaphragms with the heater structure 500. A heater 500 can be embedded in the insulation 502. A first insulation layer 502 under the heater 500 can be generated, for example thermally, by oxidation, a second insulation layer 502 can be generated by means of the heater 500 over a deposited insulating layer 502, for example a PECVD (plasma-assisted chemical gas phase deposition) or LPCVD (low pressure chemical gas phase deposition) oxide or nitride.

Figure 6:
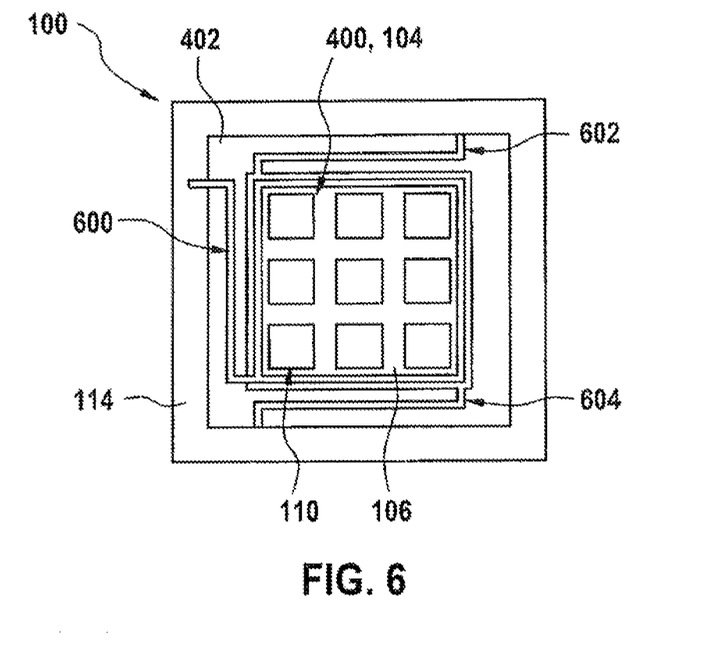
FIG. 6 shows a view from below of a microelectrochemical sensor according to an exemplary embodiment of the present disclosure.

FIG. 6 shows a view from below of a first side of a microelectrochemical sensor 100 according to an exemplary embodiment of the present disclosure. The sensor 100 corresponds to the sensor in FIG. 4. It is apparent here that the fin structure 400 is square. The fin structure 400 is formed by four webs 104 in the longitudinal direction and four webs 104 in the transverse direction. The webs 104 serve to mechanically reinforce the diaphragm. The fin structure 400 surrounds nine square partial surfaces 110 of identical size, as individual MECS diaphragms. The fin structure 400 is covered, together with the partial surfaces 110, by a rear first electrode 106. The fin structure 400 is surrounded by the insulating region 402 and is separated from the base body 114 by the insulating region 402. The insulating region 402 has a width which remains the same around the circumference. The insulating region 402 is covered by three conductor tracks 600, 602, 604. The conductor tracks 600, 602, 604 have a square S shape, a meander. The conductor tracks 600, 602, 604 run in this exemplary embodiment from a corner of the fin structure 400 perpendicularly away from an edge of the fin structure 400 over a first half of the insulating region 402. The conductor tracks 600, 602, 604 then bend at a right angle and run parallel to an edge of the fin structure 400 as far as the next corner of the fin structure 400. The length of the conductor tracks is therefore significantly increased compared to a direct connection over the insulating region 402, with the result that the flow of heat away from the flow structure 400 to the base body 114 is reduced. At the next corner, the conductor tracks 600, 602, 604 bend at a right angle again and cross a second half of the insulating region 402. The first conductor track 600 is a feed line to the first electrode 106 as an electrode terminal of the rear side. The second conductor track 602 and the third conductor track 604 are terminals for the heating element in the webs 104. The heater runs in the webs 104 between the individual MECS diaphragms 110 and is insulated from the substrate and with respect to the electrode material.

In the implementation of a selectively heated arrangement of MECS cells 110 with a heater and front and rear electrodes 106 as shown here, both the heaters 602, 604 and the electrode terminal 600 in FIG. 6 are conducted to the outside via the diaphragm 102. In order to achieve better thermal insulation and in order to reduce the thermomechanical stress which occurs, the distances of the terminals 600, 602, 604 can be lengthened by laying tangentially.

Figure 7:
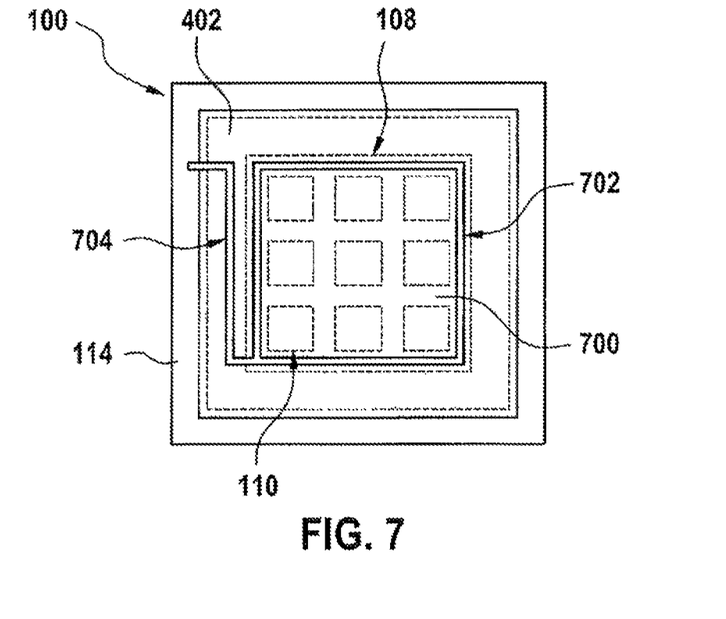
FIG. 7 shows a plan view of a microelectrochemical sensor according to an exemplary embodiment of the present disclosure.

FIG. 7 shows a plan view of a microelectrochemical sensor 100 according to an exemplary embodiment of the present disclosure. The sensor 100 corresponds to the sensor in FIG. 4. The second electrode 108 extends congruently with respect to the first electrode as illustrated in FIG. 6. The second electrode 108 makes contact with the partial surfaces 110 and a surface 700 lying opposite the webs. The insulating region 402 is not covered by the second electrode 108. The second electrode 108 has a circumferential conductor track ring 702 as an electrode terminal. The second electrode 108 is connected to the base body 114 via a fourth conductor track 704 as a feed line to the electrode terminal 702 of the front side.

The fourth conductor track 704 has a square S shape, analogous to the three conductor tracks in FIG. 6.

Figure 8:
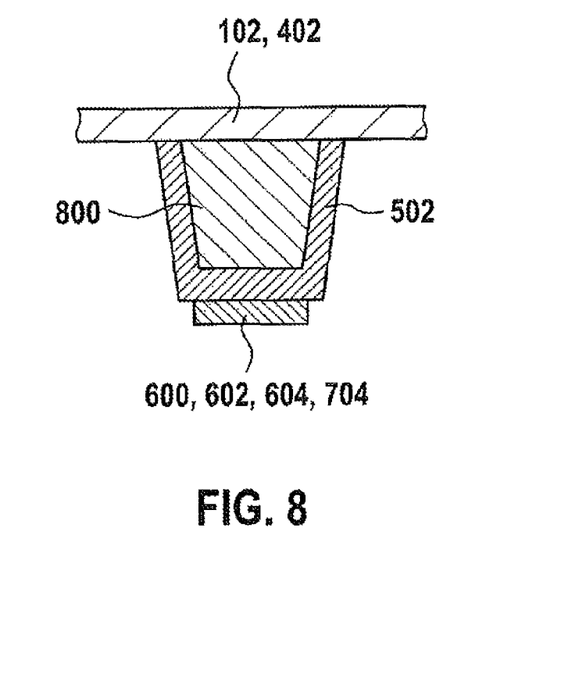
FIG. 8 shows a view of a detail of a fin of a microelectrochemical sensor according to an exemplary embodiment of the present disclosure.

FIG. 8 shows a view of a detail of a fin 800 of a microelectrochemical sensor according to an exemplary embodiment of the present disclosure. The fin 800 can be used as a substructure for the conductor tracks in FIGS. 6 and 7, for example as terminals for the heater. The fin 800 can be composed of a material of the webs. The fin 800 can be manufactured in the same working step as the webs. The fin 800 can be etched from the semiconductor material. The etching can result in a trapezoidal cross section of the fin 800. The fin 800 is arranged directly on the diaphragm 102 in the insulating region 402. The fin 800 has, like the web in FIG. 5, an edge layer 502. In the edge layer 502, the material of the fin 800 is electrically insulating. One of the conductor tracks 600, 602, 604, 704 is arranged on a side of the fin 800 facing away from the diaphragm 102.

Figure 9:
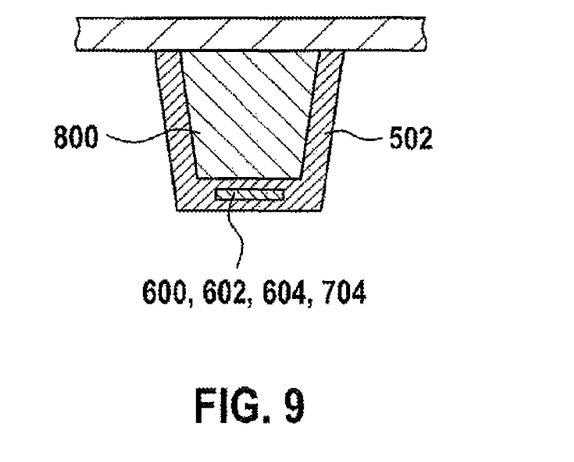
FIG. 9 shows a view of a detail of a fin of a microelectrochemical sensor according to a further exemplary embodiment of the present disclosure.

FIG. 9 shows a view of a detail of a fin 800 of a microelectrochemical sensor according to a further exemplary embodiment of the present disclosure. The fin 800 corresponds to the fin in FIG. 8. In contrast to FIG. 8, the conductor track 600, 602, 604, 704 is embedded here in the electrically insulating edge region 502 and is completely enclosed.

Figure 10:
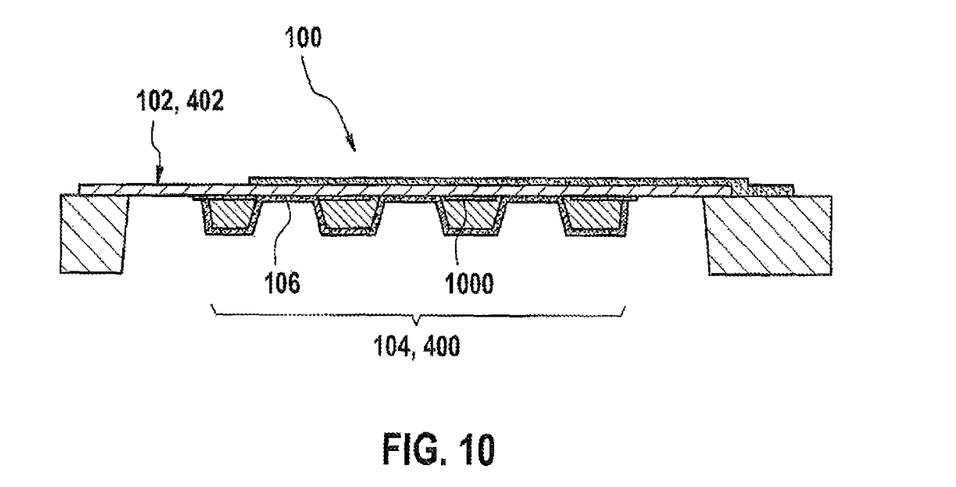
FIG. 10 shows an illustration of a microelectrochemical sensor according to a further exemplary embodiment of the present disclosure.

FIG. 10 shows an illustration of a microelectrochemical sensor 100 according to a further exemplary embodiment of the present disclosure. The sensor 100 corresponds to the sensor in FIG. 4. In contrast to FIG. 4, the webs 104 are not arranged directly on the diaphragm 102. The heating element is arranged between the diaphragm 102 and the webs 104. The heating element is embedded in an insulating layer 1000. The insulating layer 1000 is arranged directly on the diaphragm 102. The webs 104 are each arranged on the insulating layer 1000 and are electrically insulated from the diaphragm 102 by the insulating layer 1000. Furthermore, the first electrode 106 also encloses here the free edge of the fin structure 400 in FIG. 4.

FIG. 10 illustrates a further example of an implementation of a selectively heated arrangement of MECS cells 110 with heaters as a sectional diagram. Possibly present electrical conductivity of the web material can also be used here to place the sections of the lower electrode 106 in contact with one another or redundantly in contact with one another. The regions of the diaphragm 102 which are covered by the webs 104 are electrically insulated by the insulating material 1000 and are not active. The sequence of the substrate 104, insulation 1000, conductor tracks and ion-conducting material 102 permits a simplified design, and with this design the ion-conducting diaphragm 102 can also be reinforced with a continuous layer of the insulating material 1000 in the circumferential region 402.

As an alternative to the exemplary embodiments shown, the webs 104 can also be composed of a heater material through which current flows directly and which is electrically insulated with respect to the diaphragm 102 and the electrode 106.

A combination of the MECS 100 with a thermal conductivity measuring principle for the surrounding air for detecting further components (for example $CO_2$) which cannot be measured directly with the MECS 100 as a gas sensor is not illustrated in FIG. 10.

By arranging a temperature sensor on the heated diaphragm 102 and a further sensor for measuring the ambient temperature, it is also possible for a thermal conductivity measuring principle for the composition of the surrounding air to be implemented by means of the detection of the power of the heating of the MECS 100 and the temperatures at the same time as the MECS measuring principle. In this context, the temperature at the diaphragm 102 can also be detected by means of the heater, for example in the form of a resistance measurement, and furthermore the heating power and heating resistance can be measured simultaneously. The detection of the temperature or temperatures can also be carried out in such a way that mutual influencing takes place, for example at the edge of the diaphragm 102. This can be compensated by means of suitable calibration.

By means of the heater power and the temperature information it is possible to carry out a concentration measurement for gases by measuring the specific thermal conductivity. In this context, either the particle pressure or else an absolute pressure can be measured. In particular gases which have a different characteristic thermal conductivity and which cannot be detected with the MECS 100, for example, $H_2O$ or $CO_2$ or hydrocarbons, can be measured per thermal conductivity.

By means of the measurement, it is also possible for extended functional control for the MECS system 100 to be carried out, for example power modulation of the heater can therefore be carried out and the temperature of the heater can be measured. On this basis, for example changes to the diaphragm 102 of the MECS 100 can be detected or deposition or storage of moisture or condensed water.

Figure 11:
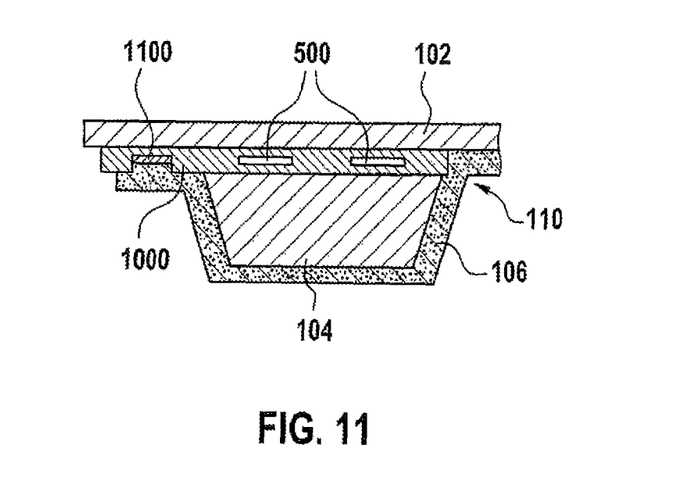
FIG. 11 shows a view of a detail of a web of a microelectrochemical sensor according to a further exemplary embodiment of the present disclosure.

FIG. 11 shows a view of a detail of a web 104 of a microelectrochemical sensor according to a further exemplary embodiment of the present disclosure. The web 104 corresponds to one of the webs in FIG. 10. This exemplary embodiment shows the insulating layer 1000 which is arranged on the diaphragm 102 and into which two heating elements 500, arranged one next to the other, and a conductor track 1100 are embedded. The web 104 is arranged on the insulating layer 1000. The conductor track 1100 serves as a feed line for the first electrode 106, which, as in FIG. 5, is arranged on the partial surfaces 110, directly on the diaphragm 102, and completely encloses the web 104. The conductor track 1100 is at least partially opened in order to make contact with the rear side electrode 106. The insulating material 1000 insulates the web 104 from the diaphragm 102.

Figure 12:
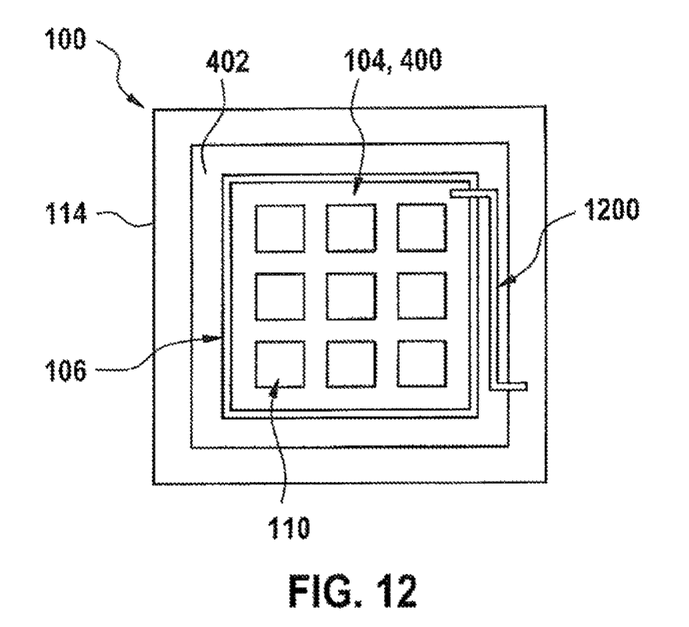
FIG. 12 shows a view from below of a microelectrochemical sensor according to a further exemplary embodiment of the present disclosure.

FIG. 12 shows a view from below of a microelectrochemical sensor 100 according to a further exemplary embodiment of the present disclosure. The sensor 100 corresponds to the sensor in FIG. 6. As in FIG. 6, the sensor 100 has nine partial surfaces 110 which are arranged in a grid and which are surrounded by webs 104 which form the fin structure 400. The first electrode 106 extends over the partial surfaces 110 and the fin structure 400. The insulating region 402 separates the partial surfaces 110 and the fin structure 400 from the base body 114. In contrast to the sensor in FIG. 6, the conductor tracks are bundled in a line 1200 which connects the fin region 400 to the base body 114 and spans the insulating region 402. The line 1200 has a square S shape, like the conductor tracks in FIG. 6.

Figure 13:
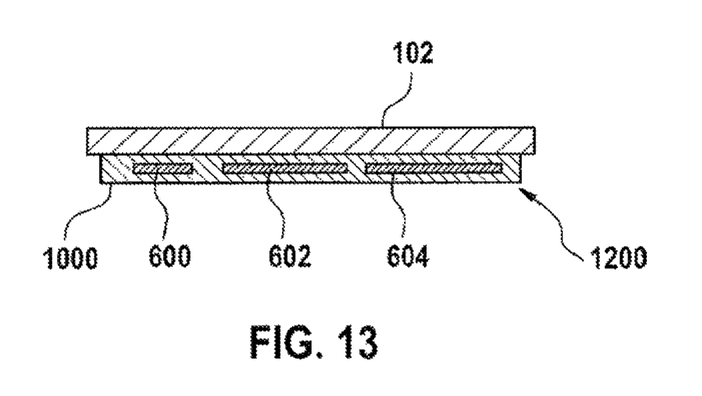
FIG. 13 shows a view of a detail of a line of a microelectrochemical sensor according to an exemplary embodiment of the present disclosure.

FIG. 13 shows a view of a detail of a line 1200 of a microelectromechanical sensor according to an exemplary embodiment of the present disclosure. The line 1200 corresponds to the line in FIG. 12. The line 1200 has an electrically insulating material 1000, in which the conductor tracks 600, 602, 604 are embedded one next to the other. The conductor tracks 600, 602, 604 run spaced apart and parallel to one another in the insulating material 1000. The insulating material 1000 is attached directly to the diaphragm 102. The conductor tracks 600, 602, 604 serve to supply the heating element and the first electrode of the sensor.

Figure 14:
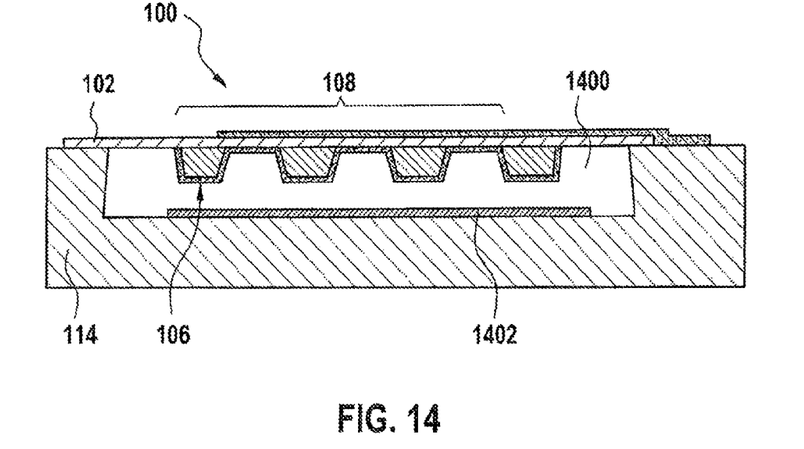
FIG. 14 shows an illustration of a microelectrochemical sensor with a chamber according to an exemplary embodiment of the present disclosure.

FIG. 14 shows an illustration of a microelectromechanical sensor 100 with a chamber 1400 according to an exemplary embodiment of the present disclosure. The sensor 100 corresponds to the sensor in FIG. 4. In addition, the base body 114 forms a cavity which is closed off or connected via a diffusion diaphragm as the chamber 1400. The first electrode 106 is arranged in the chamber 1400 as a rear side electrode for the MECS and as an electrode which can move together with the diaphragms 102 or the fin structure 400. A third electrode 1402 is arranged as a fixed electrode 1402 for measuring pressure, on a rear wall of the chamber 1400 lying opposite the first electrode 106. The chamber 1400 is of fluid-tight design. The first electrode 106 and the third electrode 1402 together form a plate capacitor. A capacitance of the plate capacitor is influenced approximately linearly by a distance between the first electrode 106 and the third electrode 1402. If the distance is smaller, the capacitance becomes larger, and vice versa. As a result of the variable capacitance, deformation of the diaphragm 102 can be detected, for example if a pressure in the chamber 1400 and/or a pressure on the second side of the diaphragm 102 changes. If a pump voltage is applied between the first electrode 106 and the second electrode 108, ions of the chemical species are then transported through the diaphragm 102. The pump voltage can be configured in such a way that the ions are transported into the chamber 1400. As a result, a pressure in the chamber 1400 can be increased. The diaphragm 102 is curved by the pressure, with the result that the distance between the first electrode 106 and the third electrode 1402 becomes larger. Since the chamber 1400 is fluid tight, tightness of the diaphragm 102 can be checked by increasing the pressure in the chamber 1400.

FIG. 14 illustrates an MECS 100 with the pressure measuring device for an inner cavity 1400 of the MECS 100 for measuring pressure and gas composition, and alternatively or additionally for functional monitoring of the MECS 100.

A simple embodiment of a pressure sensor is shown in conjunction with an MECS 100. The pressure measurement is carried out in this exemplary embodiment by measuring the capacitance between a fixed electrode 1402 and the rear side electrode 106 of the MECS 100 which moves as a function of a pressure difference between the interior space and the exterior space. The capacitance and the mechanical properties of the diaphragm 102 are a measure of the pressure difference here.

An absolute pressure can be measured in the case of a closed-off internal volume 1400. By pumping oxygen through the diaphragm 102, it is possible to vary the internal pressure with respect to the external pressure in a selective fashion, which can be used for functional control of the sensor 100. By monitoring the rise or drop in pressure with the pressure sensor 100 when pumping oxygen with the MECS element, it is possible to check the tightness of the diaphragm 102 during ongoing operation. As a result of oxygen being pumped into the internal volume 1400, a high oxygen partial pressure is generated there. The gas in the internal volume 1400 can then be used as a reference gas with respect to the ambient gas with the MECS sensor 100.

Figure 15:
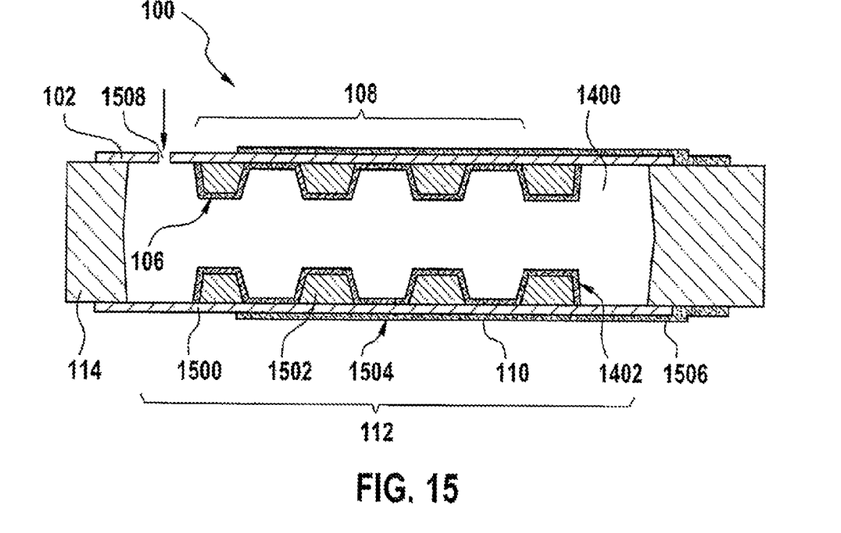
FIG. 15 shows an illustration of a microelectrochemical sensor with a chamber according to a further exemplary embodiment of the present disclosure.

FIG. 15 shows an illustration of a microelectrochemical sensor 100 with a chamber 1400 according to a further exemplary embodiment of the present disclosure. The sensor 100 has, as in FIG. 14, the chamber 1400. In contrast to FIG. 14, the cutout 112 in the base body 114 is embodied as a through-hole to a second side of the base body 114. The first side of the through-hole is closed off by the diaphragm 102. The second side of the through-hole is closed off by a second diaphragm 1500, which has a second fin structure 1502 with partial surfaces 110, the third electrode 1402, a fourth electrode 1504 and a second insulating region 1506. The second diaphragm 1500 is of analogous design to the diaphragm 102. The first electrode 106 and the third electrode 1402 can be connected, as in FIG. 14, as a plate capacitor with a variable capacitance in order to detect the distance. The diaphragm 102 has here a diffusion opening 1508. The diffusion opening 1508 makes it possible for fluid components to migrate through the diaphragm 102. If the first electrode 106 and the second electrode 108 have pump voltage applied to them in order to pump ions through the diaphragm 102 into the chamber 1400, the fluid components can diffuse through the diffusion opening 1508 through the diaphragm 102 in a direction opposite to the pumped ion stream. As a result of the diffusion, a slow pressure equalization occurs across the diaphragm 102. When the pump voltage is applied, fluid components other than the atoms or molecules of the pumped species can be rinsed out of the chamber 1400 through the diffusion opening 1508. If the pump voltage is applied continuously or regularly over a relatively long time period, a reference fluid can be produced in the chamber 1400, which reference fluid is composed completely of the atoms or molecules of the pumped species. Since the concentration of the reference fluid is known, the concentration on the other side of the diaphragm can be determined absolutely. The diffusion opening 1508 can also be arranged at another location in the chamber 1400. If both diaphragms 102, 1500 have different fluids applied to them, the concentration of the species in both fluids can be measured absolutely by means of the common reference fluid in the chamber 1400. If the sensor in FIG. 14 were also to have a diffusion opening 1508 on the chamber, a reference fluid could also be generated in the chamber 1400. For this purpose, the pumping of the ions could take place alternately with the measurement of the concentration.

The combined sensor 100 is advantageously embodied with a defined diffusion opening 1508 which is configured such that an overpressure can be generated at least temporarily in the interior space 1400 of the sensor 100. As a result, a pumping operation with increased pumping power for a tightness test can be carried out temporarily, wherein the pressure profile of the sensor 100 can be observed by means of the pressure sensor. Furthermore, by briefly pumping at least for some time it is possible to generate a high oxygen partial pressure in the interior 1400, which can serve as a reference gas volume for a lambda probe measurement.

A significant advantage with the MECS 100 for, for example, the use as the lambda sensor, is that the properties of the ion-conducting layer 102 are already adjusted during the deposition. This is a significant difference compared to the ceramic lambda probe in which the layers are initially present only as green bodies. A measurable sensor is not produced there until after baking and sintering, and after this the layers can, however, only then be limited or changed by means of complex methods.

FIG. 15 shows an exemplary cross section through an implementation of an MECS system 100 as a broadband lambda probe. The gas space at the bottom is in contact with the exhaust gas, and the gas space is connected via the sensor 100 to ambient air. A diaphragm 102, 1500 can be used as a pumping cell and the other diaphragms 102, 1500 can be used as a measuring cell or Nernst cell. A pressure which is generated temporarily by the pump cell can be measured between the two rear side electrodes 106, 1402.

As a result, gas sensors 100 for emissions of internal combustion engines, in particular also for on-board diagnosis, can be made available by the approach presented here. In particular, the sensors 100 presented here can be used for NOx detection and for measuring oxygen and oxygen-containing gases.

The exemplary embodiments which are described and shown in the figures are selected only by way of example. Different exemplary embodiments can be combined with one another completely or with respect to individual features. Features of one exemplary embodiment can be added to another.

In addition, method steps according to the disclosure can be repeated and executed in another sequence to that described.

If an exemplary embodiment comprises an "and/or" conjunction between a first feature and a second feature, this is to be understood as meaning that the exemplary embodiment according to one embodiment has both the first feature and the second feature, and according to a further embodiment it has either only the first feature or only the second feature.

What is claimed is:

1. A microelectrochemical sensor comprising:
   a diaphragm that includes:
      a first partial surface; and
      a second partial surface;
   wherein:
      the diaphragm is permeable to ions of a chemical species, at least in a region of the first partial surface and second partial surface;
      the diaphragm is positioned transversely with respect to a cutout in a base body; and
      the diaphragm closes off the cutout in a fluid tight fashion;
   a web positioned on a first side of the diaphragm between the first partial surface and the second partial surface, wherein the web is configured to adjust a temperature of the diaphragm in the region of the first partial surface and second partial surface to an operating temperature using electrical energy;
   a first electrode that includes:
      a first partial electrode; and
      a second partial electrode;
   wherein:
      the first electrode is permeable to fluid;
      the first electrode is positioned on the first side of the diaphragm, at least on the first partial surface and the second partial surface; and
      the web is configured to prevent electrical contact between the first electrode and the diaphragm in a region of the web; and
   a second electrode that includes:
      a third partial electrode; and
      a fourth partial electrode;
   wherein:
      the second electrode is permeable to fluid; and
      the second electrode is positioned on a second side of the diaphragm, at least on the first partial surface and the second partial surface.

2. The microelectrochemical sensor according to claim 1, wherein at least one of:
   the web comprises a grid, and the first partial surface and the second partial surface are enclosed by the web;
   the first partial electrode is electrically connected to the second partial electrode; and
   the third partial electrode is electrically connected to the fourth partial electrode.

3. The microelectrochemical sensor according to claim 1, wherein:
   the diaphragm includes an insulating region located around the cutout;
   the insulating region is electrode free; and
   the insulating region comprises at least one of:
      a material of the diaphragm; and
      an insulating material.

4. The microelectrochemical sensor according to claim 1, wherein:
   the web comprises a heating element configured to adjust the temperature; and
   (i) a material of the web includes an electrical resistance, wherein the material of the web is insulated from at least one of:
      the first electrode; and
      the diaphragm; or
   (ii) at least one of:
      the heating element is positioned between the web and the diaphragm; and
      the heating element is positioned between the first electrode and the web, and is electrically insulated from the first electrode and the diaphragm.

5. The microelectrochemical sensor according to claim 4, wherein:
   at least one of the first electrode, the second electrode, and the heating element is placed in contact by at least one respective conductor track; and
   the at least one respective conductor track is at least one of:
      configured to run via the insulating region to the base body; and
      electrically insulated from the diaphragm.

6. The microelectrochemical sensor according to claim 1, further comprising a temperature sensor configured to detect at least one of:
   a temperature of the diaphragm; and
   an ambient temperature.

7. The microelectrochemical sensor according to claim 1, wherein:
   the cutout is configured as a closed-off chamber; and
   a wall of the closed-off chamber located opposite the diaphragm includes a third electrode.

8. The microelectrochemical sensor according to claim 7, wherein at least one of:
   (i) the wall of the closed-off chamber located opposite the diaphragm is configured as a further diaphragm that includes:
      a further web; and
      a fourth electrode; and
   (ii) the closed-off chamber further includes a diffusion opening.

9. A method of operating a microelectrochemical sensor, comprising:
   applying an electrical pump voltage between a first electrode and a second electrode, the electrical pump voltage configured to pump ions of a chemical species through a diaphragm, wherein:
      the diaphragm is permeable to the ions, at least in a region of a first partial surface and a second partial surface;
      the diaphragm is positioned transversely with respect to a cutout in a base body;
      the diaphragm closes off the cutout in a fluid tight fashion;
      a web is positioned on a first side of the diaphragm between the first partial surface and the second partial surface;
      the web is configured to adjust a temperature of the diaphragm in the region of the first partial surface and second partial surface to an operating temperature using electrical energy;
      the first electrode is permeable to fluid, includes a first partial electrode and a second partial electrode, and is positioned on the first side of the diaphragm, at least on the first partial surface and the second partial surface;

the second electrode is permeable to fluid, includes a third partial electrode and a fourth partial electrode, and is positioned on a second side of the diaphragm, at least on the first partial surface and the second partial surface; and the web is configured to prevent electrical contact between the first electrode and the diaphragm in a region of the web.

10. The method of operating a microelectrochemical sensor according to claim 9, further comprising:

detecting at least one of:
   a capacitance between the first electrode and a third electrode; and
   a change in the capacitance; and determining a deflection of the diaphragm based at least in part upon the detecting;

wherein:
   the cutout is configured as a closed-off chamber; and
   a wall of the closed-off chamber located opposite the diaphragm includes the third electrode.

11. The method of operating a microelectrochemical sensor according to claim 10, further comprising determining a pressure on the diaphragm based at least in part upon the deflection.

12. The method of operating a microelectrochemical sensor according to claim 9, wherein the pump voltage is applied for at least one of:

a specific period; and until the deflection is greater than a predetermined value.

13. The method of operating a microelectrochemical sensor according to claim 9, further comprising at least one of:

(i) measuring an electrical voltage between the first electrode and second electrode, and detecting a first ratio of a first concentration of ions at the first electrode to a second concentration of ions at the second electrode; and (ii) measuring an electrical voltage between a third electrode and a fourth electrode, and detecting a second ratio of the first concentration of ions at the third electrode to a third concentration of ions at the fourth electrode, wherein:
   the cutout is configured as a closed-off chamber; and
      a wall of the closed-off chamber located opposite the diaphragm is configured as a further diaphragm that includes the third electrode and the fourth electrode.

14. The method of operating a microelectrochemical sensor according to claim 9, wherein:

the method is performed by a computer program executing on a device; and the computer program includes a program code configured to carry out the method.

* * * * *